United States Patent [19]

Dingerdissen et al.

[11] Patent Number: 5,763,668

[45] Date of Patent: Jun. 9, 1998

[54] PROCESS FOR AMINATING A MIXTURE OBTAINED IN CRACKING A MINERAL OIL FRACTION WITH AMMONIA OR A PRIMARY OR SECONDARY AMINE OVER SPECIFIC HETEROGENEOUS CATALYSTS

[75] Inventors: Uwe Dingerdissen, Seeheim-Jugenheim; Jürgen Herrmann, Mannheim; Karsten Eller, Lugwigshafen, all of Germany

[73] Assignee: BASF Aktiengesellschaft, Ludwigshafen, Germany

[21] Appl. No.: 675,731

[22] Filed: Jul. 3, 1996

[30] Foreign Application Priority Data

Jul. 4, 1995 [DE] Germany ............ 195 24 240.8

[51] Int. Cl.[6] .................................... C07C 209/60
[52] U.S. Cl. ............ 564/485; 546/349; 564/408; 564/445
[58] Field of Search ............ 564/408, 445, 564/485; 546/349

[56] References Cited

U.S. PATENT DOCUMENTS

| | | | |
|---|---|---|---|
| 4,375,002 | 2/1983 | Peterson et al. | 564/445 |
| 4,536,602 | 8/1985 | Deeba | 564/485 |

FOREIGN PATENT DOCUMENTS

| | | |
|---|---|---|
| 2092964 | 6/1994 | Canada. |
| 101921 | 3/1984 | European Pat. Off.. |
| 132736 | 2/1985 | European Pat. Off.. |
| 133938 | 3/1985 | European Pat. Off.. |
| 305564 | 3/1989 | European Pat. Off.. |
| 431451 | 6/1991 | European Pat. Off.. |
| 4206992 | 9/1993 | Germany. |

OTHER PUBLICATIONS

Corma et al. "Influence of theMetod of Dealumination of Y Zeolites on the Behavior for Cracking N–Heptane and Vacuum Gas–Oil", Stud. Surf. Sci. Cat., vol.37 (1987), pp. 495–503.

Brunet et al, Functionalisation of Alkenes: Catalytic Amination of Monoolefins. J. Mol. Catal. vol. 49 (1989) pp. 235–359.

Primary Examiner—Richard L. Raymond
Attorney, Agent, or Firm—John H. Shurtleff

[57] ABSTRACT

Amines are prepared by reacting a mixture obtained in the cracking of mineral oil fractions with ammonia or a primary or secondary amine of the general formula I

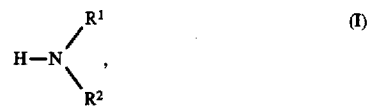

where $R^1$ and $R^2$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl or together are a saturated or unsaturated $C_2$–$C_{12}$-alkylene ene chain, at from 200° to 350° C. and from 100 to 300 bar in the presence of a heterogeneous catalyst, by a process which comprises using one or more members of the following classes as the heterogeneous catalyst:

a) zeolites
b) aluminosilicates
c) hydrothermally prepared phosphates
d) mesoporous oxides having a large surface area
e) pillared interlayered clays (PILCs)
f) amorphous oxides which are prepared by the sol-gel process
g) acid-treated sheet silicates

10 Claims, No Drawings

PROCESS FOR AMINATING A MIXTURE OBTAINED IN CRACKING A MINERAL OIL FRACTION WITH AMMONIA OR A PRIMARY OR SECONDARY AMINE OVER SPECIFIC HETEROGENEOUS CATALYSTS

The present invention relates to a process for the preparation of amines by reacting mixtures obtained in the cracking of mineral oil fractions with ammonia or a primary or secondary amine at elevated temperatures and pressures in the presence of a zeolite, an aluminosilicate, a hydrothermally prepared phosphate, oxides having a large surface area, pillared clays or acid-treated sheet silicates.

An overview of the methods for the amination of olefins is given in "Functionalisation of Alkenes: Catalytic Amination of Monoolefins", J. J. Brunet et al. J. Mol. Catal., 49 (1989), 235–259.

There are in principle two catalytic mechanisms. The olefin is coordinated via a metal complex. This activated species can be attacked by the nucleophilic amine and can form a more highly aminated product. The amine may be chemisorbed at acid centers or at metal centers (via metal amides) and may be reacted in this activated form with the olefin.

Suitable catalysts are zeolites. They have a large number of catalytically active centers in combination with a large surface area. The zeolites described differ in type and in aftertreatment (for example, thermal treatment, dealumination, acid treatment, metal ion exchange, etc.). Examples of this appear in U.S. Pat. No. 4,375,002, U.S. Pat No. 4,536,602, EP-A-305 564, EP-A-101 921 and DE-A-42 06 992.

EP-A-133 938, EP-A-431 451 and EP-A-132 736 disclose processes in which borosilicate, gallsilicate, aluminosilicate and ferrosilicate zeolites are used for the preparation of mines from olefins, and indicate the possibility of doping these zeolites with alkali metals, alkaline earth metals and transition metals.

CA-A-2 092 964 discloses a process for the preparation of amines from olefins, in which BETA-zeolites, which are defined as crystalline aluminosilicates having a certain composition with a pore size of more than 5 Å, are used. Metal-modified or halogen-modified beta-zeolites are preferably used.

The disadvantage of the abovementioned processes is the use of the olefins in pure form or in prepurified or simple mixtures.

It is an object of the present invention to remedy these disadvantages.

We have found that this object is achieved by a novel and improved process for the preparation of amines by reacting a mixture obtained in the cracking of mineral oil fractions with ammonia or primary or secondary amines of the general formula I

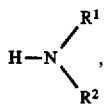

where $R^1$ and $R^2$ are each hydrogen, $C_1$–$C_{20}$-alkyl, $C_2$–$C_{20}$-alkenyl, $C_2$–$C_{20}$-alkynyl, $C_3$–$C_{20}$-cycloalkyl, $C_4$–$C_{20}$-alkylcycloalkyl, $C_4$–$C_{20}$-cycloalkylalkyl, aryl, $C_7$–$C_{20}$-alkylaryl or $C_7$–$C_{20}$-aralkyl or together are a saturated or unsaturated $C_2$–$C_{12}$-alkylene chain,
at from 200° to 350° C. and from 100 to 300 bar in the presence of a heterogeneous catalyst, which comprises using one or more members of the following classes as the heterogeneous catalysts a) zeolites
b) aluminosilicates
c) hydrothermally prepared phosphates
d) mesoporous oxides having a large surface area
e) pillared interlayered clays (PILCs)
f) amorphous oxides which are prepared by the sol-gel process
g) acid-treated sheet silicates The novel process can be carried out as follows:

Mixtures obtained in the cracking of mineral oil fractions, for example the C4-cut which is obtained on a large industrial scale in the thermal or catalytic cracking of, for example, naphtha, and ammonia or the primary or secondary amine I can be reacted at from 200° to 350° C., preferably from 220° to 330° C., particularly preferably from 230 ° to 320° C., and from 100 to 300 preferably from 120 to 300, particularly preferably from 140 to 290, bar in the presence of a zeolite, an aluminosilicate, a hydrothermally prepared phosphate, an oxide having a large surface area, a pillared clay or an acid-treated sheet silicate as the heterogeneous catalyst, for example in a pressure-resistant reactor, and the amines obtained can be isolated and the unconverted starting materials recycled.

The use of a mixture of C4-hydrocarbons from which butadiene has been removed by extraction or selective hydrogenation is also of particular interest. Such mixtures are available, for example as refined product I, in large amounts. Under suitable conditions, the isobutene contained in refined product I can be reacted selectively with ammonia or an amine to give tert-butylamine or other amines without the other hydrocarbons contained in refined product I exhibiting significant conversions. In this way, expensive removal of isobutene from the refined product I, which removal was required to date for the preparation of TBA, can be dispensed with, and there are considerable economic advantages.

The present process has a very good yield in combination with high selectivity and a high space-time yield. Furthermore, no deactivation of the catalyst has been observed.

The novel process is distinguished by the fact that a high selectivity based on desired reaction product is achieved even with a small excess of ammonia or of amine, and dimerization and/or oligomerization of the olefins used is avoided.

In an embodiment of this process, ammonia and/or an amine I, mixed together with the hydrocarbon mixtures in a molar ratio of from 1:1 to 5:1, are fed to a fixed-bed reactor and reacted at from 100 to 300 bar and from 200° to 350° C. in the gas phase or in the supercritical state.

The desired product can be obtained from the reacted mixture with the aid of known methods, for example distillation or extraction, and if necessary brought to the desired purity by means of further separation operations. The unconverted starting materials are, as a rule, preferably recycled to the reactor, and unreactive saturated hydrocarbons can readily be removed at this point.

The position of the equilibrium and hence the conversion to the desired amine is very greatly dependent on the reaction pressure chosen. High pressure favors the adduct, but pressures up to 300 bar are generally optimum for technical and economic reasons. The selectivity of the reaction is influenced to a high degree by the temperature, in addition to parameters such as ammonia/amino excess and catalyst. Although the rate of the addition reaction increases sharply with increasing temperature, competing crack and recombination reactions of the olefins contained in the mixture used are simultaneously promoted. Furthermore, for thermodynamic reasons, an increase in temperature is not advantageous. The optimum temperature with respect to conversion and selectivity is dependent on the constitution of the olefin, of the amine I used and of the catalyst and is in general from 200° to 350° C.

Suitable heterogeneous catalysts for the novel process are zeolites, such as aluminum, boron, gallium or titanium zeolites of the pentasil, faujasite, ZSM-12, EMT, SSZ-37, CIT-1, SSZ-33, SSZ-26, chinoplilolite, offretite, MCM-22, PSH-3 or BETA type, preferably H-ZSM-5, H-ZSM-11, H-aluminum-beta, H-boron-ZSM-5, H-boron-ZSM-11, H-boron-beta, H-MCM-22, H-PSH-3 and USY, or aluminosilicates or the hydrothermally prepared phosphates having a zeolite structure, such as SAPOs or AlPOs, preferably SAPO-5, AlPO-5 or SAPO-37. Mesoporous oxides having a large surface area, in particular those having BET surface areas of more than 500 m$^2$g$^{-1}$, pillared (interlayered) clays (PILCs), amorphous oxides which are prepared by the sol-gel process or acid-treated sheet silicates, such as the bleaching earths, are also suitable.

As a rule, the catalysts according to the invention are preferably used in the H form and molded with a binder in a weight ratio of from 98:2 to 40:60 to give extrudates or pellets. Suitable binders are various aluminas, preferably boehmite, amorphous aluminosilicates having an SiO$_2$/Al$_2$O$_3$ ratio of from 25:75 to 95:5, silica, preferably finely divided SiO$_2$, mixtures of finely divided SiO$_2$ and finely divided Al$_2$O$_3$, finely divided TiO$_2$ and clays. After the molding procedure, the extrudates or pellets are advantageously dried at 110° C. for 16 hours and calcined at from 300° to 500° C. for from 2 to 16 hours, it also being possible for the calcination to take place directly in the amination reactor.

In order to increase the selectivity, the life and the number of possible regenerations, various modifications may be carried out on the catalysts according to the invention.

In one method for modifying the catalysts, the unmolded catalysts or the catalysts according to the invention can be subjected to ion exchange or doping with alkali metals, such as Na and K, alkaline earth metals, such as Ca and Mg, earth metals, such as Tl, transition metals, for example Mn, Fe, Mo, Cu, Zn and Cr, noble metals and/or rare earth metals, for example La, Ce or Y.

In an advantageous embodiment, the molded catalysts according to the invention are initially taken in a flow tube and, for example, a halide, an acetate, an oxalate, a citrate or a nitrate of the metals described above, in dissolved form, is passed over at from 20° to 100° C. Ion exchange of this type can be carried out, for example, on the hydrogen, ammonium and alkali metal forms of the catalysts according to the invention.

In another possible method for applying metals to the catalysts according to the invention, the zeolite material is impregnated, for example, with a halide, an acetate, an oxalate, a citrate, a nitrate or an oxide of the metals described above, in aqueous or alcoholic solution.

Both an ion exchange and an impregnation may be followed by drying and, if desired, repeated calcination. In the case of metal-doped catalysts, an aftertreatment with hydrogen and/or with steam may be advantageous.

In a further possible method for modification, the material of the heterogeneous catalyst, in molded or unmolded form, is subjected to a treatment with acids, such as hydrochloric acid (HCl), hydrofluoric acid (HF), phosphoric acid (H$_3$PO$_4$), sulfuric acid (H$_2$SO$_4$), oxalic acid (HO$_2$C—CO$_2$H) or mixtures thereof.

In a particular embodiment, the catalyst powder is refluxed with from 0.001 to 2N, preferably from 0.05 to 0.5N, hydrofluoric acid for from 1 to 3 hours before being molded. After the product has been filtered off and thoroughly washed, it is as a rule dried at from 100° to 160° C. and calcined at from 400° to 550° C. A further particular embodiment involves an HCl treatment of the heterogeneous catalysts after they have been molded with binders. Here, the heterogeneous catalyst is treated, as a rule for from 1 to 3 hours at from 60° to 80° C., with a 3–25, in particular 12–20, % strength hydrochloric acid, then thoroughly washed, dried at from 100° to 160° C. and calcined at from 400° to 550° C.

Another possible method of modification is exchange with ammonium salts, for example with NH$_4$Cl, or with mono-, di- or polyamines. Here, the heterogeneous catalyst molded with binder is subjected to exchange continuously for 2 hours, as a rule at from 60° to 80° C., with from 10 to 25, preferably 20, % strength NH$_4$Cl solution in a solution of heterogeneous catalyst and ammonium chloride in a weight ratio of 1:15, and the product is then dried at from 100° to 120° C.

A further possible modification of the catalysts according to the invention is dealumination, in which some of the aluminum atoms are replaced by silicon or the aluminum content of the catalysts is reduced by, for example, hydrothermal treatment. Hydrothermal dealumination is advantageously followed by extraction with acids or complexing agents, in order to remove non-lattice aluminum formed. The replacement of aluminum by silicon can be effected, for example, with the aid of (NH$_4$)$_2$SiF$_6$ or SiCl$_4$. Examples of dealuminations of Y-zeolites appear in Corma et al., Stud. Surf. Sci. Catal. 37 (1987), 495–503.

For the amination of the hydrocarbon mixtures, the catalysts may be used in the form of extrudates having diameters of, for example, from 1 to 4 mm or in the form of pellets having a diameter of, for example, from 3 to 5 mm.

A fluidizable material having a size of from 0.1 to 0.8 mm can be obtained from the catalyst, which for example has been molded to give extrudates, by milling and sieving.

In the compound I, R$^1$ and R$^2$ are each hydrogen,

C$_1$–C$_{20}$-alkyl, preferably C$_1$–C$_{12}$–alkyl, particularly preferably C$_1$–C$_8$-alkyl, such as methyl, ethyl, n-propyl, isopropyl, n-butyl, isobutyl, sec-butyl, tert-butyl, n-pentyl, isopentyl, n-hexyl, isohexyl, n-heptyl, isoheptyl, n-octyl or isooctyl, C$_2$–C$_{20}$-alkenyl, preferably C$_2$–C$_{12}$-alkenyl, particularly preferably C$_2$–C$_8$-alkenyl, such as vinyl or allyl, C$_2$–C$_{20}$-alkynyl, in particular C$_2$H or propargyl, C$_3$–C$_{20}$-cycloalkyl, preferably C$_3$–C$_{12}$-cycloalkyl, particularly preferably C$_5$–C$_8$-cycloalkyl, such as cyclopentyl, cyclohexyl, cycloheptyl or cyclooctyl, C$_4$–C$_{20}$-alkylcycloalkyl, preferably C$_4$–C$_{12}$-alkylcycloalkyl, particularly preferably C$_5$–C$_{10}$-alkylcycloalkyl, C$_4$–C$_{20}$-cycloalkylalkyl, preferably C$_4$–C$_{12}$-cycloalkylalkyl, particularly preferably C$_5$–C$_{10}$-cycloalkylalkyl, aryl, such as phenyl, 1-naphthyl or 2-naphthyl, preferably phenyl, C$_7$–C$_{20}$-alkylaryl, preferably C$_7$–C$_{16}$-alkylaryl, preferably C$_7$–C$_{12}$-alkylphenyl, such as 2-methylphenyl, 3-methylphenyl, 4-methylphenyl, 2-ethylphenyl, 3-ethylphenyl or 4-ethylphenyl, C$_7$–C$_{20}$-aralkyl, preferably C$_7$–C$_{16}$-aralkyl, preferably C7–C$_{12}$-phenalkyl, such as phenylmethyl, 1-phenylethyl or 2-phenylethyl, or together are a saturated $C_2$-$C_{12}$-alkylene chain, preferably a $C_3$-$C_8$-alkylene chain, particularly preferably —$(CH_2)_3$—, —$(CH_2)_4$—, —$(CH_2)_5$—, —$(CH_2)_6$— or —$(CH_2)_7$—, in particular —$(CH_2)_3$— or —$(CH_2)_4$—, or together are an unsaturated $C_2$-$C_{20}$-alkylene chain, particularly preferably an unsaturated $C_3$-$C_8$-alkylene chain, particularly preferably —CH=CH—CH=CH—.

EXAMPLES

Extrusion of catalyst

Catalyst A 40 g of boehmite and 2 g of formic acid were added to 60 g of beta-zeolite (from Uetikon). The mixture was compacted in a kneader and kneaded with the careful addition of water (not more than 65 ml). The kneading time was 60 minutes. 2 mm extrudates were produced in an extruder at a pressure of 80 bar and were dried for 16 hours at 120° C. and then calcined for 16 hours at 500° C.

Catalyst B 40 g of boehmite and 2 g of formic acid were added to 60 g of ZSM-5 zeolite (from Uetikon, PZ-2/60). The mixture was compacted in a kneader and kneaded with the careful addition of water (64 ml). The kneading time was 40 minutes. 2 mm extrudates were produced in an extruder at a pressure of 55 bar and were dried for 16 hours at 120° C. and then calcined for 16 hours at 450° C.

Aminations

Examples 1 to 10

The continuous preparation was carried out using a high-pressure reactor which had a length of 2 mm and an internal diameter of 24 mm, was heated by means of an aluminum block and was equipped with triple internal temperature measurement and with a pressure relief means. In each case, 60 ml of catalyst were installed and the upper part of the reactor tube was filled with porcelain rings. Olefin-containing mixture comprising $C_4$-cuts and ammonia as fed in from above.

The analysis of the reacted mixtures was carried out by gas chromatography and, if desired, additionally by distillation.

In a tube reactor (6 mm internal diameter), a mixture of ammonia and refined product I [composition in mol %: 12% of butane, 4.4% of isobutane, 43.6% of isobutene, 26% of 1-butene, 8.1% of trans-2-butene and 5.9% of cis-2-butene] in a molar ratio of $NH_3$ to refined product I of from 0.7:1 to 1.3:1 was reacted under iso-thermal conditions at from 270° to 300° C. and 280 bar. The reaction products were analyzed in a gas chromatography.

The results obtained with the various catalysts are summarized in Table 1. They show that it is possible selectively to convert isobutene in a mixture of $C_4$-hydrocarbons with ammonia into tert-butylamine. Under the chosen conditions, the other amines are converted only to a very slight extent into sec-butylamine (2-aminobutane). By changing the pressure and temperature, however, it is possible to find conditions under which this reaction, too, takes place.

TABLE 1

| Ex. No. | Catalyst | $NH_3$/refined product % | Temp. (°C.) | Pressure [°C.] | UHSV [g/gh] | Butane | Iso-butane | Σ Iso-butane | trans-Butane | cis-Butane | tert-Butyl-amino (TBA) | sec-Butyl-amine | Selectivity (TBA) | Conversion of refined product % |
|---|---|---|---|---|---|---|---|---|---|---|---|---|---|---|
| 1 | A | 1.3:1 | 270 | 280 | 0.5 | 20.1 | 3.7 | 57.7 | 6.2 | 5.9 | 13.7 | 0 | 96.2 | 14.3 |
| 2 | A | 1.3:1 | 270 | 260 | 1 | 11.6 | 4.2 | 59.6 | 5.3 | 5.8 | * | 0 | 97.5 | 10.5 |
| 3 | A | 1.3:1 | 270 | 280 | 1.7 | 11.0 | 4.2 | 60.6 | 8.2 | 6 | 8.7 | 0 | 97.7 | 8.9 |
| 4 | B | 1.3:1 | 270 | 280 | 0.5 | 11.8 | 4.2 | 50.6 | 8.2 | 6 | 10.8 | 0.1 | 97 | 11.1 |
| 5 | B | 0.7:1 | 280 | 260 | 0.5 | 11.8 | 4.3 | 61.1 | 8.1 | 5.9 | 0 | 0.3 | 91.8 | 8.7 |
| 6 | B | 0.7:1 | 280 | 280 | 1 | 11.8 | 4.1 | 61.2 | 8.2 | 6 | 7.1 | 0.2 | 86.7 | 8.2 |
| 7 | B | 1.3:1 | 280 | 280 | 1 | 11.9 | 4.2 | 60.2 | 8.2 | 6 | 9.1 | 0.2 | 96.1 | 9.5 |
| 8 | B | 1.3:1 | 270 | 280 | 1 | 11.7 | 4.1 | 61.5 | 8.3 | 6.1 | 8.1 | 0.1 | 96.6 | 8.4 |
| 9 | B | 1.3:1 | 300 | 250 | 1 | 12 | 4.3 | 63 | 8.3 | 6 | 5.9 | 0.5 | 90.2 | 6.4 |
| 10 | B | 1.3:1 | 270 | 280 | 2 | 11.9 | 4.2 | 61.4 | 8.3 | 6 | 8.1 | 0 | 98 | 8.2 |

*)not separated on the GC column used

We claim:

1. A process for the preparation of amines which comprises reacting isobutene in a mixture obtained in the cracking of mineral oil fractions with ammonia or a primary or secondary amine of the formula I

(I)

where

R¹ and R² are each hydrogen, $C_1$-$C_{20}$-alkyl, $C_2$-$C_{20}$-alkenyl, $C_2$-$C_{20}$-alkynyl, $C_3$-$C_{20}$-cycloalkyl, $C_4$-$C_{20}$-alkyl- cycloalkyl, $C_4$-$C_{20}$-cycloalkylalkyl, aryl, $C_7$-$C_{20}$- alkylaryl or $C_7$-$C_{20}$-aralkyl or together are a saturated or unsaturated $C_2$-$C_{12}$-alkylene chain, at from 200° to 350° C. and from 100 to 300 bar in the presence of a heterogeneous catalyst selected from one or more members of the following classes as the:

a) zeolites
b) aluminosilicates
c) hydrothermally prepared phosphates
d) mesoporous oxides having a large surface area
e) pillared interlayered clays (PILCS)
f) amorphous oxides which are prepared by the sol-gel process and
g) acid-treated sheet silicates.

2. A process as claimed in claim 1, wherein an aluminum, boron, gallium or titanium zeolite of the pentasil, faujasite, EMT or BETA type is used as the heterogeneous catalyst.

3. A process as claimed in claim 1, wherein said mixture obtained in the cracking of a mineral oil fraction as the reactant contains isobutene, cis-2-butene, trans-2-butene, 1-butene, isobutane and n-butane.

4. A process as claimed in claim 1, wherein said heterogeneous catalyst is, a zeolite in the H form.

5. A process as claimed in claim 1, wherein said heterogeneous catalyst is treated with an acid selected from the group consisting of hydrochloric acid, hydrofluoric acid, phosphoric acid, sulfuric acid oxalic acid or mixtures thereof.

6. A process as claimed in claim 1, wherein said heterogeneous catalyst is doped with at least one transition metal.

7. A process as claimed in claim 1, wherein said heterogeneous catalyst is doped with at least one rare earth element.

8. A process as claimed in claim 1, wherein said heterogeneous catalyst is doped with at least one element selected from the group consisting of alkali metals, alkaline earth metals and rare earth metals.

9. A process as claimed in claim 1, wherein said heterogeneous catalyst is used in its ammonium form.

10. A process as claimed in claim 1, wherein said heterogeneous catalyst has been molded with a binder and calcined at from 300° to 600° C.

* * * * *